United States Patent [19]
Cohen et al.

[11] Patent Number: 4,740,470
[45] Date of Patent: * Apr. 26, 1988

[54] BIOLOGICALLY FUNCTIONAL MOLECULAR CHIMERAS

[75] Inventors: Stanley N. Cohen, Menlo Park; Herbert W. Boyer, Mill Valley, both of Calif.

[73] Assignee: The Board of Trustees of the Leland Stanford, Jr. University, Stanford, Calif.

[*] Notice: The portion of the term of this patent subsequent to Dec. 2, 1997 has been disclaimed.

[21] Appl. No.: 602,294

[22] Filed: Apr. 20, 1984

Related U.S. Application Data

[63] Continuation of Ser. No. 959,288, Nov. 9, 1978, Pat. No. 4,468,464, which is a continuation of Ser. No. 687,430, May 17, 1976, abandoned, which is a continuation-in-part of Ser. No. 520,691, Nov. 4, 1974, abandoned.

[51] Int. Cl.[4] .................... C12N 15/00; C12N 5/00; C12N 1/20; C12N 1/00; C12P 19/34
[52] U.S. Cl. ............................ 435/172.3; 435/91; 435/320; 435/240.2; 435/253; 935/27; 935/31; 935/32
[58] Field of Search ................... 435/172.3, 91, 317, 435/253, 240, 320, 240.2; 935/27, 31, 32

[56] References Cited

PUBLICATIONS

Maniatis, Cell Biology, vol. 3, pp. 563-608 (1980).
Mentz et al, PNAS USA, vol. 69, pp. 3370-3374, Nov. 1972.
Jackson et al., PNAS USA, vol. 69, pp. 2904-2909, Oct. 1972.
Keeton, Biological Sciences, Pub. by Norton & Co., Inc., New York, pp. 88-90 (1967).
Hicks et al., Nature, vol. 269, pp. 265-267 (1977).
Hinnen et al., PNAS USA, vol. 75, pp. 1929-1933 (1978).
Buggs, Nature, vol. 275, pp. 104-109 (1978).
"The Integrated State of Viral DNA in SV40-Transformed Cells", J. Sambrook et al., PNAS, (1968), 60: 1288-1295.
"Bacterial Conjugation", Curtiss, Am. Rev. Microbiol., (1969), 23: 69-135.
"Transduction of Lysogeny in Escherichia coli", Jacob, Virology, (1955), 1;207-220.
"Kinetics of Renaturation of DNA", Wetmur & Davidson, J. Molec. Biol., (1968), 31: 349-370.
"Size Distribution of Circular DNA from petite-mutant Yeast Lacking pDNA", Clark-Walker, Eur. J. Biochem., (1973), 32: 263-267.
"Isolation of Circular DNA from a Mitochondrial Fraction from Yeast", Clark-Walker, PNAS, (1972), 69: 388-392.
"A Map of the Restriction Targets in Yeast 2 Micron Plasmid DNA Cloned on Bacteriophage Lambda", Beggs et al., Molec. gen. Genet., (1976), 148: 287-294.
"Bidirectional Replication of Simian Virus 40 DNA", Danna and Nathans, PNAS, (1972), 69: 3097-3100.
"Virus-Specific RNA in Cells Productively Infected or Transformed by Polyoma Virus", Benjamin, J. Molec. Biol., (1966), 16: 359-373.
"Transduction in Escherichia coli K-12", Morse et al., Genetics, (1956), 41: 142-156.
"Construction of Biologically Functional Bacterial Plasmids in Vitro", Cohen et al., PNAS, (1973), 70: 3240-3244.
"Nonchromosomal Antibiotic Resistance in Bacteria: Genetic Transformation of Escherichia coli by R-Factor DNA", Cohen et al., PNAS, (1972), 69: 2110-2114.
"Calcium-Dependent Bacteriophage DNA Infection", Mandel et al., J. Mol. Biol., (1970) 53: 159-162.
"Transfection of Escherichia coli Spheroplasts", Henner et al., J. Virol., (1973), 12: 741-747.
"Viable Molecular Hybrids of Bacteriophage Lambda and Eukaryotic DNA", Thomas et al., PNAS, (1974), 71: 4579-4583.
"Extrachromosomal Inheritance in Bacteria", Novick, Bac. Rev., (1969), 33: 210-263.
Federal Register, vol. 44, No. 71, Wednesday Apr. 11, 1979, Notices.

Primary Examiner—Alvin E. Tanenholtz
Attorney, Agent, or Firm—Bertram I. Rowland

[57] ABSTRACT

Method and compositions are provided for replication and expression of exogenous genes in microorganisms. Plasmids or virus DNA are cleaved to provide linear DNA having ligatable termini, which are bound to a gene having complementary termini, to provide a biologically functional replicon with a desired phenotypical property. The replicon is inserted into a microorganism cell by transformation. Isolation of the transformants provides cells for replication and expression of the DNA molecules present in the modified plasmid. The method provides a convenient and efficient way to introduce genetic capability into microorganisms for the production of nucleic acids and proteins, such as medically or commercially useful enzymes, which may have direct usefulness, or may find expression in the production of drugs, such as hormones, antibiotics, or the like, fixation of nitrogen, fermentation, utilization of specific feedstocks, or the like.

The invention was supported by generous grants of NIH, NSF and the American Cancer Society.

23 Claims, No Drawings

BIOLOGICALLY FUNCTIONAL MOLECULAR CHIMERAS

CROSS-REFERENCE TO RELATED APPLICATIONS

This application is a continuation of application Ser. No. 959,288, filed Nov. 9, 1978, now U.S. Pat. No. 4,468,464; which is a continuation of application Ser. No. 687,430, filed May 17, 1976, now abandoned; which is a continuation-in-part of application Ser. No. 520,691, filed Nov. 4, 1974, now abandoned.

BACKGROUND OF THE INVENTION

1. Field of the Invention

Although transfer of plasmids among strains of *E. coli* and other Enterobacteriaceae has long been accomplished by conjugation and/or transduction, it has not been previously possible to selectively introduce particular species of plasmid DNA into these bacterial hosts or other microorganisms. Since microorganisms that have been transformed with plasmid DNA contain autonomously replicating extrachromosomal DNA species having the genetic and molecular characteristics of the parent plasmid, transformation has enabled the selective cloning and amplification of particular plasmid genes.

The ability of genes derived from totally different biological classes to replicate and be expressed in a particular microorganism permits the attainment of interspecies genetic recombination. Thus, it becomes practical to introduce into a particular microorganism, genes specifying such metabolic or synthetic functions as nitrogen fixation, photosynthesis, antibiotic production, hormone synthesis, protein synthesis, e.g. enzymes or antibodies, or the like—functions which are indigenous to other classes of organisms—by linking the foreign genes to a particular plasmid or viral replicon.

2. Brief Description of the Prior Art

References which relate to the subject invention are Cohen, et al., Proc. Nat. Acad, Sci., USA, 69, 2110 (1972); ibid, 70, 1293 (1973); ibid, 70, 3240 (1973); ibid, 71, 1030 (1974); Morrow, et al., Proc. Nat. Acad. Sci., 71, 1743 (1974); Novick, Bacteriological Rev., 33, 210 (1969); and Hershfeld, et al., Proc. Nat. Acad. Sci., in press; Jackson, et al., ibid, 69, 2904 (1972);

SUMMARY OF THE INVENTION

Methods and compositions are provided for genetically transforming microorganisms, particularly bacteria, to provide diverse genotypical capability and producing recombinant plasmids. A plasmid or viral DNA is modified to form a linear segment having ligatable termini which is joined to DNA having at least one intact gene and complementary ligatable termini. The termini are then covalently bound to form a "hybrid" plasmid molecule which is used to transform susceptible and compatible microorganisms. After transformation, the cells are grown and the transformants harvested. The newly functionalized microorganisms may then be employed to carry out their new function; for example, by producing proteins which are the desired end product, or metabolites of enzymic conversion, or be lysed and the desired nucleic acids or proteins recovered.

DESCRIPTION OF THE SPECIFIC EMBODIMENTS

The process of this invention employs novel plasmids, which are formed by covalently inserting DNA having one or more intact genes into a plasmid in such a location as to permit retention of an intact replicator locus and systems (replicon) to provide a recombinant plasmid molecule. The recombinant plasmid molecule will be referred to as a "hybrid" plasmid or plasmid "chimera." The plasmid chimera contains genes that are capable of expressing at least one phenotypical property. The plasmid chimera is used to transform a susceptible and competent microorganism under conditions where transformation occurs. The microorganism is then grown under conditions which allow for separation and harvesting of transformants that contain the plasmid chimera.

The process of this invention will be divided into the following stages:

I. preparation of the recombinant plasmid or plasmid chimera;

II. transformation or preparation of transformants; and

III. replication and transcription of the recombinant plasmid in transformed bacteria.

I. PREPARATION OF PLASMID CHIMERA

In order to prepare the plasmid chimera, it is necessary to have a plasmid, which can be cleaved to provide an intact replicator locus and system (replicon), where the linear segment has ligatable termini or is capable of being modified to introduce ligatable termini. A small number of such plasmids presently exist. Of particular interest are those plasmids which have a phenotypical property, which allow for ready separation of transformants from the patent microorganism. The plasmid will be capable of replicating in a microorganism, particularly a bacterium, which is susceptible to transformation. Various unicellular microorganisms can be transformed, such as bacteria, fungii and algae. That is, those unicellular organisms which are capable of being grown in cultures or fermentation. Since bacteria are for the most part the most convenient organisms to work with, bacteria will be hereinafter referred to as exemplary of the other unicellular organisms. Bacteria, which are susceptible to transformation, include members of the Enterobacteriaceae, such as strains of *Escherichia coli;* Salmonella; Bacillaceae, such as *Bacillus subtilis;* Pneumococcus; Streptococcus, and *Haemophilus influenzae.*

A wide variety of plasmids may be employed of greatly varying molecular weight. Normally, the plasmids employed will have molecular weights in the range of about $1 \times 10^6$ to $50 \times 10^6$d, more usually from about 1 to $20 \times 10^6$d, and preferably, from about 1 to $10 \times 10^6$d, the desirable plasmid size is determined by a number for factors. First, the plasmid must be able to accommodate a replicator locus and one or more genes that are capable of allowing replication of the plasmid. Secondly, the plasmid should be of a size which provides for a reasonable probability of recircularization with the foreign gene(s) to form the recombinant plasmid chimera. Desirably, a restriction enzyme should be available, which will cleave the plasmid without inactivating the replicator locus and system associated with the replicator locus. Also, means must be provided for providing ligatable termini for the plasmid, which are complementary to the termini of the foreign gene(s) to allow fusion of the two DNA segments.

Another consideration for the recombinant plasmid is that it be compatible with the bacterium to be transformed. Therefore, the original plasmid will usually be derived from a member of the family to which the bacterium belongs.

The original plasmid should desirably have a phenotypical property which allows for the separation of transformant bacteria from parent bacteria. Particularly useful is a gene, which provides for survival selection. Survival selection can be achieved by providing resistance to a growth inhibiting substance or providing a growth factor capability to a bacterium deficient in such capability.

Conveniently, genes are available, which provide for antibiotic or heavy metal resistance or polypeptide resistance, e.g. colicin. Therefore, by growing the bacteria on a medium containing a bacteriostatic or bacteriocidal substance, such as an antibiotic, only the transformants having the antibiotic resistance will survive. Illustrative antibiotics include tetracycline, streptomycin, sulfa drugs, such as sulfonamide, kanamycin, neomycin, penicillin, chloramphenicol, or the like.

Growth factors include the synthesis of amino acids, the isomerization of substrates to forms which can be metabolized or the like. By growing the bacteria on a medium which lacks the appropriate growth factor, only the bacteria which have been transformed and have the growth factor capability will clone.

One plasmid of interest derived from *E. coli* is referred to as pSC101 and is described in Cohen, et al., Proc. Nat. Acad. Sci., USA, 70, 1293 (1972), (referred to in that article as Tc6-5). Further description of this particular plasmid and its use is found in the other articles previously referred to.

The plasmid pSC101 has a molecular weight of about $5.8 \times 10^6$d and provides tetracycline resistance.

Another plasmid of interest is colicinogenic factor EI (ColE1), which has a molecular weight of $4.2 \times 10^6$d, and is also derived from *E. coli*. The plasmid has a single EcoRI substrate site and provides immunity to colicin E1.

In preparing the plasmid for ligation with the exogenous gene, a wide variety of techniques can be provided, including the formation of or introduction of cohesive termini. Flush ends can be joined. Alternatively, the plasmid and gene may be cleaved in such a manner that the two chains are cleaved at different sites to leave extensions at each and which serve as cohesive termini. Cohesive termini may also be introduced by removing nucleic acids from the opposite ends of the two chains or alternatively, introducing nucleic acids at opposite ends of the two chains.

To illustrate, a plasmid can be cleaved with a restriction endonuclease or other DNA cleaving enzyme. The restriction enzyme can provide square ends, which are then modified to provide cohesive termini or can cleave at different, but adjacent, sites on the two strands, so as to provide cohesive termini directly.

Where square ends are formed such as, for example, by HIN (*Haemophilus influenzae* RII) or pancreatic DNAse, one can ligate the square ends or alternatively one can modify the square ends by chewing back, adding particular nucleic acids, or a combination of the two. For example, one can employ appropriate transferases to add a nucleic acid to the 5' and 3' ends of the DNA. Alternatively, one can chew back with an enzyme, such as a λ-exonuclease, and it is found that there is a high probability that cohesive termini will be achieved in this manner.

An alternative way to achieve a linear segment of the plasmid with cohesive termini is to employ an endonuclease such as EcoRI. The endonuclease cleaves the two strands at different adjacent sites providing cohesive termini directly.

With flush ended molecules, a $T_4$ ligase may be employed for linking the termini. See, for example, Scaramella and Khorana, J. Mol. Biol. 72: 427–444(1972) and Scaramella, DNAS 69: 3389(1972), whose disclosure is incorporated herein by reference.

Another way to provide ligatable termini is to cleave employing DNAse and $Mn^{++}$ as reported by Lai and Nathans, J. Mol. Biol. 89: 179(1975).

The plasmid, which has the replicator locus, and serves as the vehicle for introduction of a foreign gene into the bacterial cell, will hereafter be referred to as "the plasmid vehicle."

It is not necessary to use plasmid, but any molecule capable of replication in bacteria can be employed. Therefore, instead of plasmid, viruses may be employed, which will be treated in substantially the same manner as the plasmid, to provide the ligatable termini for joining to the foreign gene.

If the production of cohesive termini is by restriction endonuclease cleavage, the DNA containing the foreign gene(s) to be bound to the plasmid vehicle will be cleaved in the same manner as the plasmid vehicle. If the cohesive termini are produced by a different technique, an analogous technique will normally be employed with the foreign gene. (By foreign gene is intended a gene derived from a source other than the transformant strain.) In this way, the foreign gene(s) will have ligatable termini, so as to be able to be covalently bonded to the termini of the plasmid vehicle. One can carry out the cleavage or digest of the plasmids together in the same medium or separately, combine the plasmids and recirculate the plasmids to form the plasmid chimera in the absence of active restriction enzyme capable of cleaving the plasmids.

Descriptions of methods of cleavage with restriction enzymes may be found in the following articles: Greene, et al., *Methods in Molecular Biology*, Vol. 9, ed. Wickner, R. B., (Marcel Dekker, Inc., New York), "DNA Replication and Biosynthesis"; Mertz and Davis, 69, Proc. Nat. Acad. Sci., USA, 69, 3370 (1972);

The cleavage and non-covalent joining of the plasmid vehicle and the foreign DNA can be readily carried out with a restriction endonuclease, with the plasmid vehicle and foreign DNA in the same or different vessels. Depending on the number of fragments, which are obtained from the DNA endonuclease digestion, as well as the genetic properties of the various fragments, digestion of the foreign DNA may be carried out separately and the fragments separated by centrifugation in an appropriate gradient. Where the desired DNA fragment has a phenotypical property, which allows for the ready isolation of its transformant, a separation step can usually be avoided.

Endonuclease digestion will normally be carried out at moderate temperatures, normally in the range of 10 to 40° C. in an appropriately buffered aqueous medium, usually at a pH of about 6.5 to 8.5. Weight percent of total DNA in the reaction mixture will generally be about 1 to 20 weight percent. Time for the reaction will vary, generally being from 0.1 to 2 hours. The amount of endonuclease employed is normally in excess of that required, normally being from about 1 to 5 units per 10 μg of DNA.

Where cleavage into a plurality of DNA fragments results, the course of the reaction can be readily followed by electrophoresis. Once the digestion has gone to the desired degree, the endonuclease is inactivated by heating above about 60° C. for five minutes. The digestion mixture may then be worked up by dialysis, gradient separation, or the like, or used directly.

The plasmid vehicle and foreign DNA fragments are then allowed to combine to form hydrogen bonds and recircularize. This process is referred to as annealing and DNA ligation. An appropriate buffered medium is employed containing the DNA fragments, DNA ligase, and appropriate cofactors. The temperature employed initially for annealing will be about −5 to 15° C. When DNA segments hydrogen bond, the DNA ligase will be able to introduce a covalent bond between the two segments. Where the two ends of each of the segments are hydrogen bonded to one another, they may be ligated to form a circularized recombinant plasmid. The mole ratio of the two segments will generally be in the range of 1-5:5-1. The particular temperature for annealing will depend upon the binding strength of the cohesive termini. While 0.5 to 2 or more days have been employed for annealing, it is believed that only a short period of 0.5 to 6 hours may be sufficient, since annealing and ligation can occur under ligating conditions. The time employed for the annealing will vary with the temperature employed, the nature of the salt solution, as well as the nature of the sticky ends or cohesive termini.

The foreign DNA can be derived from a wide variety of sources. The DNA may be derived from eukaryotic or prokaryotic cells, viruses, and bacteriophage. The fragments employed will generally have molecular weights in the range of about 0.5 to $20 \times 10^6$d, usually in the range of 1 to $10 \times 10^6$d. The DNA fragment may include one or more genes or one or more operons.

Desirably, if the plasmid vehicle does not have a phenotypical property which allows for isolation of the transformants, the foreign DNA fragment should have such property.

The covalent joining can be achieved in conventional ways employing a DNA ligase. Ligation is conveniently carried out in an aqueous solution (pH, 6-8) at temperatures in the range of 5° to 40° C. The concentration of the DNA will generally be from about 10 to 100 μg/ml. A sufficient amount of the DNA ligase or other ligating agent, e.g. $T_4$ ligase, is employed to provide a convenient rate of reaction, generally ranging from 5 to 50 U/ml. Small amounts of a protein, e.g. albumin, may be added at concentrations of 10 to 200 μg/ml. The ligation with DNA ligase is carried out in the presence of $Mg^{++}$ at about 1-10 mM.

At the completion of the ligation, the solution may be chilled and is ready for use in transformation.

In accordance with the subject invention, plasmids may be prepared which have replicons and genes which could be present in bacteria as a result of normal mating of bacteria. However, the subject invention provides a technique, whereby a replicon and gene can coexist in a plasmid, which is capable of being introduced into a unicellular organism, which could not exist in nature. The first type of plasmid which cannot exist in nature is a plasmid which derives its replicon from one organism and the exogenous gene from another organism, where the two organisms do not exchange genetic information. In this situation, the two organisms will either be eukaryotic or prokaryotic. Those organisms which are able to exchange genetic information by mating are well known. Thus, prior to this invention, plasmids having a replicon and one or more genes from two sources which do not exchange genetic information would not have existed in nature. This is true, even in the event of mutations, and induced combinations of genes from different strains of the same species. For the natural formation of plasmids formed from a replicon and genes from different microorganisms it is necessary that the microorganisms be capable of mating and exchanging genetic information.

In the situation, where the replicon comes from a eukaryotic or prokaryotic cell, and at least one gene comes from the other type of cell, this plasmid heretofore could not have existed in nature. Thus, the subject invention provides new plasmids which cannot naturally occur and can be used for transformation of unicellular organisms to introduce genes from other unicellular organisms, where the replicon and gene could not previously naturally coexist in a plasmid.

Besides naturally occurring genes, it is feasible to provide synthetic genes, where fragments of DNA may be joined by various techniques known in the art. Thus, the exogenous gene may be obtained from natural sources or from synthetic sources.

The plasmid chimera contains a replicon which is compatible with a bacterium susceptible of transformation and at least one foreign gene which is directly or indirectly bonded through deoxynucleotides to the replicon to form the circularized plasmid structure. As indicated previously, the foreign gene normally provides a phenotypical property, which is absent in the parent bacterium. The foreign gene may come from another bacterial strain, species or family, or from a plant or animal cell. The original plasmid chimera will have been formed by in vitro covalent bonding between the replicon and foreign gene. Once the originally formed plasmid chimera has been used to prepare transformants, the plasmid chimera will be replicated by the bacterial cell and cloned in vitro by growing the bacteria in an appropriate growth medium. The bacterial cells may be lysed and the DNA isolated by conventional means or the bacteria continually reproduced and allowed to express the genotypical property of the foreign DNA.

Once a bacterium has been transformed, it is no longer necessary to repeat the in vitro preparation of the plasmid chimera or isolate the plasmid chimera from the transformant progeny. Bacterial cells can be repeatedly multiplied which will express the genotypical property of the foreign gene.

One method of distinguishing between a plasmid which originates in vivo from a plasmid chimera which originates in vitro is the formation of homoduplexes between an in vitro prepared plasmid chimera and the plasmid formed in vivo. It will be an extremely rear event where a plasmid which originates in vivo will be the same as a plasmid chimera and will form homoduplexes with plasmid chimeras. For a discussion of homoduplexes, see Sharp, Cohen and Davidson, J. Mol. Biol., 75, 235 (1973), and Sharp, et al, ibid, 71, 471, (1972).

The plasmid derived from molecular cloning need not homoduplex with the in vitro plasmid originally employed for transformation of the bacterium. The bacterium may carry out modification processes, which will not affect the portion of the replicon introduced which is necessary for replication nor the portion of the exogenous DNA which contains the gene providing the genotypical trait. Thus, nucleotides may be introduced or excised and, in accordance with naturally occurring mating and transduction, additional genes may be introduced. In addition, for one or more reasons, the plasmids may be modified in vitro by techniques which are known in the art. However, the plasmids obtained by molecular cloning will homoduplex as to those parts which relate to the original replicon and the exogenous gene.

II. TRANSFORMATION

After the recombinant plasmid or plasmid chimera has been prepared, it may then be used for the transformation of bacteria. It should be noted that the annealing and ligation process not only results in the formation of the recombinant plasmid, but also in the recircularization of the plasmid vehicle. Therefore, a mixture is obtained of the original plasmid, the recombinant plasmid, and the foreign DNA. Only the original plasmid and the DNA chimera consisting of the plasmid vehicle and linked foreign DNA will normally be capable of replication. When the mixture is employed for transformation of the bacteria, replication of both the plasmid vehicle genotype and the foreign genotype will occur with both genotypes being replicated in those cells having the recombinant plasmid.

Various techniques exist for transformation of a bacterial cell with plasmid DNA. A technique, which is particularly useful with *Escherichia coli,* is described in Cohen, et al., ibid, 69, 2110 (1972). The bacterial cells are grown in an appropriate medium to a predetermined optical density. For example, with *E. coli* strain C600, the optical density was 0.85 at 590 nm. The cells are concentrated by chilling, sedimentation and washing with a dilute salt solution. After centrifugation, the cells are resuspended in a calcium chloride solution at reduced temperatures (approx. 5°–15° C.), sedimented, resuspended in a smaller volume of a calcium chloride solution and the cells combined with the DNA in an appropriately buffered calcium chloride solution and incubated at reduced temperatures. The concentration of $Ca^{++}$ will generally be about 0.01 to 0.1M. After a sufficient incubation period, generally from about 0.5–3.0 hours, the bacteria are subjected to a heat pulse generally in the range of 35° to 45° C. for a short period of time; namely from about 0.5 to 5 minutes. The transformed cells are then chilled and may be transferred to a growth medium, whereby the transformed cells having the foreign genotype may be isolated.

An alternative transformation technique may be found in Lederberg and Cohen, J. Bacteriol., 119, 1072 (1974), whose disclosure is incorporated herein by reference.

III. REPLICATION AND TRANSCRIPTION OF THE PLASMID

The bacterial cells, which are employed, will be of such species as to allow replication of the plasmid vehicle. A number of different bacteria which can be employed, have been indicated previously. Strains which lack indigenous modification and restriction enzymes are particularly desirable for the cloning of DNA derived from foreign sources.

The transformation of the bacterial cells will result in a mixture of bacterial cells, the dominant proportion of which will not be transformed. Of the function of cells which are transformed, some significant proportion, but normally a minor proportion, will have been transformed by the recombinant plasmid. Therefore, only a very small fraction of the total number of cells which are present will have the desired phenotypical characteristics.

In order to enhance the ability to separate the desired bacterial clones, the bacterial cells, which have beeen subjected to transformation, will first be grown in a solution medium, so as to amplify the absolute number of the desired cells. The bacterial cells may then be harvested and streaked on an appropriate agar medium. Where the recombinant plasmid has a phenotype, which allows for ready separation of the transformed cells from the parent cells, this will aid in the ready separation of the two types of cells. As previously indicated, where the genotype provides resistance to a growth inhibiting material, such as an antibiotic or heavy metal, the cells can be grown on an agar medium containing the growth inhibiting substance. Only available cells having the resistant genotype will survive. If the foreign gene does not provide a phenotypical property, which allows for distinction between the cells transformed by the plasmid vehicle and the cells transformed by the plasmid chimera, a further step is necessary to isolate the replicated plasmid chimera from the replicated plasmid vehicle. The steps include lysing of the cells and isolation and separation of the DNA by conventional means or random selection of transformed bacteria and characterization of DNA from such transformants to determine which cells contain molecular chimeras. This is accomplished by physically characterizing the DNA by electrophoresis, gradient centrifugation or electron microscopy.

Cells from various clones may be harvested and the plasmid DNA isolated from these transformants. The plasmid DNA may then be analyzed in a variety of ways. One way is to treat the plasmid with an appropriate restriction enzyme and analyze the resulting fragments for the presence of the foreign gene. Other techniques have been indicated above.

Once the recombinant plasmid has been replicated in a cell and isolated, the cells may be grown and multiplied and the recombinant plasmid employed for transformation of the same or different bacterial strain.

The subject process provides a technique for introducing into a bacterial strain a foreign capability which is genetically mediated. A wide variety of genes may be employed as the foreign genes from a wide variety of sources. Any intact gene may be employed which can be bonded to the plasmid vehicle. The source of the gene can be other bacterial cells, mammalian cells, plant cells, etc. The process is generally applicable to bacterial cells capable of transformation. A plasmid must be available, which can be cleaved to provide a linear segment having ligatable termini, and an intact replicator locus and system, preferably a system including a gene which provides a phenotypical property which allows for easy separation of the transformants. The linear segment may then be annealed with a linear segment of DNA having one or more genes and the resulting recombinant plasmid employed for transformation of the bacteria.

By introducing one or more exogenous genes into a unicellular organism, the organism will be able to produce polypeptides and proteins ("poly(amino acids)") which the organism could not previously produce. In some instances the poly(amino acids) will have utility in themselves, while in other situations, particularly with enzymes, the enzymatic product(s) will either be useful in itself or useful to produce a desirable product.

One group of poly(amino acids) which are directly useful as hormones. Illustrative hormones includes parathyroid hormone, growth hormone, gonadotropins (FSH, luteinizing hormone, chroionogonadatropin, and glycoproteins), insulin, ACTH, somatostatin, prolactin, placental lactogen, melanocyte stimulating hormone, thyrotropin, parathyroid hormone, calcitonin, enkephalin, and angiotensin.

Other poly(amino acids) of interest include serum proteins, fibrinogin, prothrombin, thromboplastin, globulin e.g. gamma-globulins or antibodies, heparin, antihemophilia protein, oxytocin, albumins, actin, myosin, hemoglobin, ferritin, cytochrome, myoglobin, lactoglobulin, histones, avidin, thyroglobulin, interferon, kinins and transcortin.

Where the gene or genes produce one or more enzymes, the enzymes may be used for fulfilling a wide variety of functions. Included in these functions are nitrogen fixation, production of amino acids e.g. polyiodothyronine, particularly thyroxine, vitamins, both water and fat soluble vitamins, antimicrobial drigs, chemotherapeutic agents e.g. antitumor drugs, polypeptides and proteins e.g. enzymes from apoenzymes and hormones from prohormones, diagnostic reagents, energy producing combinations e.g. photosynthesis and hydrogen production, prostaglandins, steroids, cardiac glycosides, coenzymes, and the like.

The enzymes may be individually useful as agents separate from the cell for commercial applications, e.g. in detergents, synthetic transformations, diagnostic agents and the like. Enzymes are classified by the I.U.B. under the classification as I. Oxidoreductases; II. Transferases; III. Hydrolases; IV. Lyases; V. Isomerases; and VI. Ligases.

EXPERIMENTAL

In order to demonstrate the subject invention, the following experiments were carried out with a variety of foreign genes.

(All temperatures not otherwise indicated are Centrigrade. All percents not otherwise indicated are percents by weight.)

EXAMPLE A

A. Preparation of pSC101 Plasmid

Covalently closed DNA was sheared with a Virtis stainless steel microshaft blade in a one milliliter cup. The DNA was sheared at 2,000 r.p.m. for 30 minutes in TEN buffer solution (0.02M Tris-HCl (pH 8.0)-1mM EDTA (pH 8.0)-0.02M NaCl), while chilled at 0°–4°.

The sheared DNA sample was subjected to sucrose gradient sedimentation at 39,500 r.p.m. in a Spinco SW 50.1 rotor at 20°. A 0.12 ml fraction was collected on a 2.3 cm diameter circle of Whatman No. 3 filter paper, dried for 20 minutes and precipitated by immersion of the disc in cold 5% trichloroacetic acid, containing 100 $\mu$g/ml thymidine. The precipitate was filtered and then washed once with 5% trichloroacetic acid, twice with 99% ethanol and dried.

B. Generalized Transformation Procedure

*E. coli* strain C600 was grown at 37° in H1 medium to an optical density of 0.85 at 590 nm. At this point the cells were chilled quickly, sedimented and washed once in 0.5 volume 10mM NaCl. After centrifugation, the bacteria were resuspended in half the original volume of chilled 0.03M calcium chloride, kept at 0° for 20 minutes, sedimented, and then resuspended in 0.1 of the original volume of 0.03M of calcium chloride solution. Chilled DNA samples in TEN buffer were supplemented with 0.1M calcium chloride to a final concentration of 0.03M.

0.2 ml of competent cells treated with calcium chloride was added to 0.1 ml of DNA solution with chilled pipets and an additional incubation was done for 60 minutes at 0°. The bacteria were then subjected to a heat pulse at 42° for two minutes, chilled, and then either plated directly onto nutrient agar containing appropriate antibiotics or, where indicated, diluted 10 times in L-broth and incubated at 37° before plating. The cell survival is greater than 50% after calcium chloride treatment and heat pulse. Drug resistance was assayed on nutrient agar plates with the antibiotics indicated in specific experiments.

EXAMPLE I

Construction of Biologically Functional Bacterial Plasmids in vitro

A. Covalently closed R6-5 plasmid DNA was cleaved by incubation at 37° for 15 minutes in a 0.2 ml reaction mixture containing DNA (40 $\mu$g/ml, 100mM Tris.HCl (pH 7.4)), 5mM MgCl$_2$, 50mM NaCl, and excess (2U) EcoRI endonuclease in 1 $\mu$l volume. An additional incubation at 60° for 5 minutes was employed to inactivate the endonuclease.

The resulting mixture of plasmid fragments was employed for transformation of *E. coli* strain C600 in accordance with the procedure previously described. A single clone was examined further which was selected for resistance to kanamycin and was also found to carry resistance to neomycin and sulfonamide, but not to tetracycline, chloramphenicol, or streptomycin after transformation of *E. coli* by EcoRI generated DNA fragments of R6-5. Closed circular DNA obtained from this isolate (plasmid designation pSC102) by CsCl-ethidium bromide gradient centrifugation has an S value of 39.5 in neutral sucrose gradients.

Treatment of pSC102 plasmid DNA with EcoRI restriction endonuclease in accordance with the above-described procudure resulted in the formation of 3 fragments that were separable by electrophoresis in agarose gels. Intact pSC102 plasmid DNA and pSC101 plasmid DNA a 27S species having a calculated molecular weight of $5.8 \times 10.^6$d), which had been separately purified by dye-buoyant density centrifugation, were treated with EcoRI endonuclease followed by annealing at 0°–2° for about six hours. The mixture was then subjected to ligation with pSC101 and pSC102 in a ratio of 1:1 respectively, by ligating for 6 hours at 14° in 0.2 ml reaction mixtures containing 5mM MgCl$_2$, 0.1mM NAD, 100 $\mu$g/ml of bovine-serum albumin (BSA), 10mM ammonium sulphate (pH 7.0), and 18 U/ml of DNA ligase. (J. Mertz and Davis, Proc. Nat. Acad. Sci., USA, 69, 3370 (1972); and Modrich, et al., J. Biol. Chem., 248, 7495 (1973). Ligated mixtures were incubated at 37° for 5 minutes and then chilled in ice water. Aliquots containing 3.3–6.5 $\mu$g/ml of total DNA were used directly for transformation.

Transformation of *E. coli* strain C600 was carried out as previously described. For comparison purposes, transformation was also carried out with a mixture of pSC101 and pSC102 plasmid DNA, which had been subjected to EcoRI endonuclease, but not DNA ligase. The antibiotics used for selection were tetracycline (10 μg/ml) and kanamycin (25 μg/ml). The results are reported as transformants per microgram of DNA. The following table indicates the results.

TABLE I

Transformation of *E. coli* C600 by a mixture of pSC101 and pSC102 DNA

| Treatment of DNA | Transformation frequency for antibiotic resistance markers | | |
|---|---|---|---|
| | Tetracycline | Kanamycin | Tetracycline + kanamycin |
| None | $2 \times 10^5$ | $1 \times 10^5$ | $2 \times 10^2$ |
| EcoRI | $1 \times 10^4$ | $1.1 \times 10^3$ | $7 \times 10^1$ |
| EcoRI + DNA ligase | $1.2 \times 10^4$ | $1.3 \times 10^3$ | $5.7 \times 10^2$ |

Kanamycin resistance in the R65 plasmid is a result of the presence of the enzyme kanamycin monophosphotransferase. The enzyme can be isolated from the bacteria by known procedures and employed in an assay for kanamycin in accordance with the procedure described in Smith, et al., New England J. Medicine, 286, 583 (1972).

In the preparation for the enzyme extracts, the *E. coli* are grown in ML-broth and harvested in a late logarithm phase of growth. The cells are osmotically shocked (see Nossal, et al., J. Biol. Chem., 241, 3055 (1966), washed twice at room temperature with 10 ml 0.01M Tris and 0.03M NaCl, pH 7.3, and the pellet suspended in 10 ml 20% sucrose, $3 \times 10^3$M EDTA and 0.033M Tris (pH 7.5), stirred for 10 minutes at room temperature and centrifuged at 16,000 g for 5 minutes. The pellet is then suspended in 2 ml of cold $5 \times 10^{-4}$M MgCl$_2$, stirred for 10 minutes at 2° and centrifuged at 26,000 g for 10 minutes to yield a supernatant fluid referred to as the osmotic shockate. The solution should be stored at $-20°$ or lower. (See Benveneste, et al., FEBS Letters, 14 293 (1971)).

The osmotic shockate may then be used in accordance with the procedure of Smith, et al, supra.

EXAMPLE II

Genome Construction between Bacterial Species in vitro: Replication and Expression of Staphylococcus Plasmid Genes in *E. coli*

*S. aureus* strain 8325 contains the plasmid pI258, which expresses resistance to penicillin, erythromycin, cadmium and mercury. (Lindberg, et al, J. Bacteriol., 115, 139 (1973)). Covalently closed circular pSC101 and pI258 plasmid DNA were separately cleaved by incubation at 37° for 15 minutes in 0.2 ml reaction mixtures by EcoRI endonuclease in accordance with the procedure described previously. Aliquots of the two cleaved species were mixed in a ratio of 3 μg of pI258:1 μg of pSC101 and annealed at 2°–4° for 48 hours. Subsequent ligation was carried out for six hours at 14° as described previously and aliquots containing 3.3–6.5 μg/ml of total DNA were used directly in the transformation as described previously.

Other transformations were carried out employing the two plasmids independently and a mixture of the two plasmids. Selection of transformants was carried out at antibiotic concentrations for tetracycline (Tc, 25 μg/ml) or pencillin (Pc, 250 U/ml). The transformation was carried out with *E. coli* strain C600 r$_K^-$m$_K^-$. The following table indicates the results.

TABLE II

Transformation of C600 r$_K^-$m$_K^-$ by pSC101 and pI258 Plasmid DNA

| DNA | Transformants/μg DNA | |
|---|---|---|
| | Tc | Pc |
| PSC101 closed circular | $1 \times 10^6$ | <3 |
| pI258 closed circular | <3.6 | <3.6 |
| pSC101 + pI258 untreated | $9.1 \times 10^5$ | <5 |
| pSC101 + pI258 EcoRI-treated | $4.7 \times 10^3$ | 10 |

The above table demonstrates that bacteria can be formed which have both tetracycline resistance and penicillin resistance. Thus, one can provide the phenotypical property penicillin resistance in bacteria from DNA, which is indigenous to another biological organism. One can thus use *E. coli* for the production of the enzyme, which imparts penicillin resistance to bacteria, and assay for penicillin in a manner similar to that employed for kanamycin. Penicillinase is used for destrying penicillin in blood serum of patients treated with penicillin in order to determine whether pathogenic organisms whose growth is inhibited by penicillin may be present.

EXAMPLE III

Replication and Transcription of Eukaryotic DNA in *E. coli*

The amplified ribosomal DNA (rDNA) coding for 18S and 28S ribosomal RNA of the South African toad, *Xenopus laevis* was used as a source of eukaryotic DNA for these experiments. Dawid, et al., J. Mol. Biol., 51, 341 (1970). *E. coli-X. laevis* recombinant plasmids were constructed in vitro as follows:

The reaction mixture (60 μl) contained 100mM Tris HCl (pH 7.5) 50mM NaCl, 5mM MgCl$_2$, 1.0 μg of pSC101 plasmid DNA and 2.5 μg of *X.laevis* rDNA, and excess EcoRI restriction endonuclease (1 μl, 2 U). After a 15 minute incubation at 37°, the reaction mixture was placed at 63° for 5 minutes to inactivate EcoRI endonuclease. The product was then refrigerated at 0.5° for 24 hours, to allow association of the short cohesive termini.

The reaction mixture for ligation of phosphodiester bonds was adjusted to a total volume of 100 μl and contained in addition to the components of the endonuclease reaction, 30mM Tris.HCl (pH 8.1), 1mM sodium EDTA, 5mM MgCl$_2$, 3.2nM NAD, 10mM ammonium sulphate, 5 μg BSA, and 9U of *E. coli* DNA ligase. All components were chilled to 5° before their addition to the reaction mixture. The ligase reaction mixture was incubated at 14° for 45 minutes, and then at 0.5° for 48 hours. Additional NAD and ligase were added and the mixture incubated at 15° for 30 minutes and then for 15 minutes at 3720 . The ligated DNA was used directly in the plasmid transformation procedure previously described. The DNA was used to transform *E. coli* strain C600 r$_K^-$m$_K^-$ and tetracycline resistant transformants ($3.3 \times 10^3$/μg of pSC101 DNA) were selected and numbered consecutively CD1, CD2, etc. Plasmid DNA was isolated from a number of the transformants.

$^{32}$P-labeled 18S and 28S *X. laevis* rRNA were hybridized with DNA obtained from the plasmids CD4, CD18, CD30, and CD42. CD4 DNA annealed almost equally with both the 18S and 28S rRNA species. CD18 plasmid hybridized principally with 28S *X. laevis* rRNA, while the DNA of plasmids CD30 and CD42 annealed primarily with 18S rRNA. These data indicate that portions of the *X. laevis* rDNA were, in fact, incorporated into a plasmid recombinant with pSC101, which was capable of transforming *E. coli*, so as to be capable of replicating *X. laevis* rDNA.

Transcription of *X. laevis* DNA was also carried out in *E. coli* minicells. The minicell producing *E. coli* strain P678-54 was transformed with plasmid DNA isolated from *E. coli* strain C600 $r_K^- m_K^-$ containing CD4, CD 18, or CD42. Many cells containing the plasmids were isolated and incubated with [³H] uridine; RNA purified from such minicells was hybridized with *X. laevis* rDNA immobilized on nitrocellulose membranes in order to determine whether the *X. laevis* rDNA linked to the pSC101 replicon is transcibed in *E. coli*. The results in the following table show the RNA species capable of annealing with purified *X. laevis* rDNA are synthesized in *E. coli* minicells carrying the recombinant plasmids CD4, CD18, and CD42, but not by minicells carrying the pSC101 plasmid alone.

Minicells containing plasmids were isolated as described by Cohen, et al., Nature New Biol., 231, 249 (1971). They were incubated with [³H] uridine (50 μCi/ml, 30 Ci/mol) as described by Roozen, et al., J. Bacteriol., 107, 21 (1971) for 10 minutes at 37°. Minicells collected by centrifugation were resuspended in Tris.HCl (20mM, pH 7.5)-5mM MgCl₂-1mM EDTA pH 8.0 and rapidly frozen and thawed 3 times. RNA was extracted as described in Cohen, et al., J. Mol. Biol., 37, 387 (1968). Hybridization assays were carried out in nitrocellulose membranes as described in Cohen, et al., ibid, at saturating levels of pSC101 DNA. Hybridizations involving *X. laevis* DNA were not performed at DNA excess. Counts bound to blank filters (5-10 c.p.m.) were subtracted from experimentally determined values. ³H count eluted from filters containing *X. laevis* DNA were rendered acid soluble by ribonuclease A 20 μg/ml, 0.30M NaCl-0.030M sodium citrate, 1 hour, 37°. The following table indicates the results.

TABLE III

| Plasmid carried by minicells | [³H] RNA synthesized by *E. coli* minicells | | |
|---|---|---|---|
| | Input cpm | [³H] RNA counts hybridized to | |
| | | *X. laevis* rDNA | pSC101 DNA |
| | | 0.2 μg    0.4 μg | 18 μg |
| CD42 | 4810 | 905 (19%)    1436 (30%) | 961 (20%) |
| CD18 | 3780 | 389 (10%)    — | 1277 (34%) |
| CD4 | 5220 | 789 (15%)    — | 1015 (19%) |
| pSC101 | 4170 | 0 (0%)    — | 1500 (36%) |

EXAMPLE IV

Plasmid ColE1 as a Molecular Vehicle for Cloning and Amplification of Trp Operon In a volume of 200 μl (100mM Tris.HCl (pH 7.5)-5mM MgCl₂-50mM NaCl), 5.7 μg of ColE1 (*E. coli* JC411Thy−/ColEl) (Clewell, et al., Proc. Nat. Acad. Sci., USA, 62, 1159 (1969) and 6.0 μg DNA from bacteriophage φ80pt190 (Deeb, et al., Virology, 31, 289 (1967) were digested to completion with homogeneously purified EcoRI endonuclease, monitoring the digestion by electrophoresis of the fragments in an agarose gel. The endonuclease was inactivated by heating at 65° for 5 minutes, the digest dialyzed overnight against 5mM Tris.HCl, pH 7.6, and the sample concentrated to 50 μl. The fragments were ligated as described in Dugaiczyk, et al., Biochemistry, 13, 503 (1974) at a concentration of 75 pmoles/ml of fragments.

Transformation was carried out as previously described except that the cells were grown to $A_{590}=0.600$ and following exposure to DNA were incubated in L-broth for 90 minutes. The cells were collected and resuspended in 10mM NaCl before plating. Cells employed as recipients for the transformations were *E. coli* strains C600 trpR′, ΔtrpE5(MV1), C600 trpR⁻ trpE 10220 recA(MV2), C600 ΔtrpE5(MV10) and C600 ΔtrpE5 recA(MV12). (trpR⁻ is the structural gene for the trp repressor and ΔtrpE5 is a trp operon deletion entirely within trpE and removing most of the gene.) Approximately 2 μg of the DNA was used to transform the cells.

Cultures were plated on Vogel-Bonner agar supplemented with 50 μg/ml of the non-selective amino acids, 0.2% glucose and 5 μg/ml of required vitamins. Transformants to colicin immunity were initially selected on a lawn of a culture of a mutant strain carrying ColE1. Clones were then selected for their ability to grow in the absence of tryptophan. Cells capable of producing tryptophan were isolated, which could be used for the production of exogenous tryptophan. The subject example demonstrates the introduction of a complete operon from foreign DNA to provide a transformant capable of replicating the operon and transcribing and translating to produce enzymes capable of producing an aromatic amino acid.

It is evident from the above results, that both DNA from a eukaryotic source and RNA transcribed from the eukaryotic DNA can be formed in a bacterial cell and isolated. Thus, the subject process provides a simple technique for producing large amounts of eukaryotic DNA and/or RNA without requiring the reproduction and maintenance of the eukaryotic organism or cells. The employment of DNA for production of ribosomal RNA is merely illustrative of using a genome from a eukaryotic cell for formation of a recombinant plasmid for replication in a bacteria. Genomes from a eukaryotic cell for formation of genotypical properites, such as the production of enzymes, could have equivalently been used. As evidenced by the transformation with DNA from a bacteriophage, an entire operon can be introduced into a bacterial cell and the cell becomes capable of its transcription, translation, and production of a functional gene product. Thus, a wide variety of auxotrophic properites can be introduced into a bacterial cell.

In accordance with the subject invention, DNA vehicles are provided, which are covalently closed circular extrachromosomal replicons or genetic elements, including plasmids and viral DNA. THe vehicles generally will have molecular weights in the range of about 1 to $20 \times 10^6$ and are characterized by having an intact replicon, which includes a replicator locus and gene. The vehicle is capable of cleavage by a restriction enzyme to provide a linear segment having an intact replicon and cohesive termini, which may be directly obtained by the cleavage or by subsequent modification of the termini of the linear segment. The vehicle will be capable of transforming a bacterial cell and to that extent is compatible with the cell which will provide replication and translation. Preferably, the vehicle will have a phenotypical property which will allow for segregation of the transformant cells. Phenotypical properites include resistance to growth inhibiting materials, such as antibiotics, peptides and heavy metals, morphological properites, color, or the like, and production of growth factors, e.g. amino acids.

The vehicle is combined with DNA indigenous to a biological organism other than the cell which provides replication and provides a genotypical or phenotypical property which is alien to the cell. The source of the DNA can be prokaryotic or eukaryotic, thus including bacteria, fungi, vertebrates, e.g. mammals and the like.

The plasmid vehicle and the alien DNA having complementary cohesive termini can be annealed together and covalently linked to provide a recombinant plasmid, which is capable of transforming a bacterial cell, so as to be capable of replication, transcription, and translation. As a result, a wide variety of unique capabilities can be readily introduced into bacteria, so as to provide convenient ways to obtain nucleic acids and to study nucleic acids from a foreign host. Thus, the method provides the ability to obtain large amounts of a foreign nucleic acid from bacteria in order to be able to study the function and nature of the nucleic acid. In addition, the subject method provides means for preparing enzymes and enzymic products from bacteria where the natural host is not as convenient or efficient a source of such product. Particularly, bacteria may allow for more ready isolation of particular enzymes, uncontaminated by undesirble contaminants, which are present in the original host. In addition, the products of the enzymic reactions may be more readily isolated and more efficiently produced by a transformant than by the original host. Besides enzymes, other proteins can be produced such as antibodies, antigens, albumins, globulins, glycoproteins, polysaccharides, and the like.

Although the foregoing invention has been described in some detail by way of illustration and example for purpsoes of clarity of understanding, it will be obvious that certain changes and modifications may be practiced within the scope of the appended claims.

What is claimed is:

1. A method for replicating biologically functional circular recombinant DNA molecules in transformed host cells, which comprises:
   (1) preparing biologically functional circular recombinant DNA molecules by: joining first and second DNA linear segments, said first and second DNA segments having termini of a predetermined character at least in part complementary, at least one of said first and second DNA linear segments having a gene for a phenotypical trait, said first DNA linear segment having an intact extrachromosmal replicon recognized by said host cell, and said second DNA linear segment having foreign DNA derived from a source which does not exchange genetic information with said host cells;
   (2) transforming said host cells with said biologically functional recombinant DNA molecules;
   (3) growing said host cells under appropriate nutrient conditions; and
   (4) isolating said transformant cells with said biologically functional recombinant DNA molecules by means of said phenotypical trait imparted by said biologically functional recombinant DNA molecules.

2. A method according to claim 1 wherein said host cells are unicellular organisms.

3. A method according to claim 1, wherein said host cells are prokaryotic organisms.

4. A method according to claims 1, 2 or 3 wherein said foreign DNA of said segment includes an intact gene capable of expression in said host cells, and including the additional step of growing said isolated transformant cells in an appropriate medium, whereby said intact gene is expressed and protein produced.

5. A method for producing foreign RNA from biologically functional circular recombinant DNA molecules in transformed host cells, which comprises:
   (1) preparing biologically functional circular recombinant DNA molecules by: joining first and second DNA linear segments, said first and second DNA segments having termini of a predetermined character at least in part complementary, at least one of, said first and second linear DNA segments having a gene for a phenotypical trait, said first DNA linear segment having an intact extrachromsomal replicon recognized by said host cells, and said second DNA linear segment having foreign DNA derived from a source which does not exchange genetic information with said host cells;
   (2) transforming said host cells with said biologically functional recombinant DNA molecules;
   (3) growing said host cells under appropriate nutrient conditions; and
   (4) isolating said RNA containing transformant cells with said biologically functional recombinant DNA molecules by means of said phenotypical trait imparted by said biologically functional recombinant DNA molecules.

6. A method for replicating biologically functional circular recombinant DNA molecules in transformed host cells, which comprises:
   (1) preparing biologically functional circular recombinant DNA molecules by: joining first and second DNa linear segments, said first and second DNA segments having termini of a predetermined character at least in part complementary, at least one of said first and second DNA linear segments having a gene for a phenotypical trait, said first DNA linear segment having an intact replicon recognized by said host cells from plasmid or viral DNA, and said second DNA linear segment having foreign DNA derived from a source which does not exchange genetic information with said host cells;
   (2) transforming said host cells with said biologically functional recombinant DNA molecules;
   (3) growing said host cells under appropriate nutrient conditions; and
   (4) isolating said transformant cells with said biologically functional recombinant DNA molecules by means of said phenotypical trait imparted by said biologically functional recombinant DNA molecules.

7. A method according to claim 6, wherein said host cells are unicellular organisms.

8. A method according to claim 6, wherein said host cells are prokaryotic organisms.

9. As an article of manufacture, a cloned biologically functional circular recombinant DNA molecule capable of selection and replication in a host cell comprising: a first DNA segment containing an intact extrachromsomal replicon recognized by said host cell, said first segment being joined to a second DNA segment having foreign DNA derived from a source which does not exchange genetic information with said host cell.

10. An article of manufacture according to claim 9, wherein said host cell is a unicellular organism.

11. An article of manufacture according to claim 9, wherein said host cell is a prokaryotic organism.

12. As an article of manufacture, a cloned biologically functional circular recombinant DNA molecule capable of selection and replication in a host cell comprising: a first DNA segment containing an intact replicon recognized by said host cell from plasmid or viral DNA joined to a second DNA segment comprising a foreign gene capable of expression in said host cell wherein said foreign gene is derived from a source which does not exchange genetic information with said host cell.

13. An article of manufacture according to claim 12, wherein said host cell is a unicellular organism.

14. An article of manufacture according to claim 12, wherein said host cell is a prokaryotic organism.

15. An article of manufacture according to claims 12, 13, or 14, wherein said gene has as a phenotypical property expression of an enzyme.

16. As an article of manufacture, a cloned biologically functional circular recombinant DNA molecule capable of selection and replication in a host cell comprising: cloned copies of a first DNA segment containing an intact extrachromsomal replicon recognized by said host cell from a plasmid or viral DNA joined to a second DNA segment comprising a foreign gene capable of expression in said host cell, wherein said foreign gene is derived from a source which does not exchange genetic information with said host cell.

17. A transformant cell comprising a biologically functional circular recombinant DNA molecule capable of selection and replication in said cell, said DNA molecule comprising: a first DNA segment containing an intact extrachromsomal replicon recognized by said cell, said first segment being joined to a second DNA segment having foreign DNA, wherein said foreign DNA is derived from a source which does not exchange genetic information with said host cell.

18. A transformant cell according to claim 17, wherein said cell is a unicellular organism.

19. A transformant cell according to claim 17, wherein said cell is a prokaryotic organism.

20. A transformant cell comprising a biologically functional circular recombinant DNA molecule capable of selection and replication in said cell, said DNA molecule comprising: a first DNA segment containing an intact extrachromsomal replicon recognized by said cell from plasmid or viral DNA, said first segment being joined to a second DNA segment comprising a foreign gene capable of expression in said cell wherein said foreign gene is derived from a source which does not exchange genetic information with said host cell.

21. A transformant cell according to claim 20, wherein said cell is a unicellular organism.

22. A transformant cell according to claim 20, wherein said cell is a prokaryotic organism.

23. A transformant cell according to claims 20, 21, or 22 wherein said cell includes the expression product of said foreign gene.

* * * * *